US006844151B1

(12) United States Patent
Dale

(10) Patent No.: US 6,844,151 B1
(45) Date of Patent: *Jan. 18, 2005

(54) METHODS FOR PRODUCTION OF ARRAYS WITH MODIFIED OLIGONUCLEOTIDE AND POLYNUCLEOTIDE COMPOSITIONS

(75) Inventor: Roderic M. K. Dale, Wilsonville, OR (US)

(73) Assignee: Oligos Etc. Inc., Wilsonville, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/408,761

(22) Filed: Sep. 29, 1999

(51) Int. Cl.[7] .............................. C12Q 1/68; C12N 15/00

(52) U.S. Cl. ........................ 435/6; 536/23.1; 536/24.3; 536/25.4

(58) Field of Search ...................... 435/6, 5; 536/24.5, 536/23.1, 24.3, 25.4

(56) References Cited

U.S. PATENT DOCUMENTS

| | | | |
|---|---|---|---|
| 5,376,528 A | * 12/1994 | King et al. .................... | 435/6 |
| 5,436,327 A | 7/1995 | Southern et al. | |
| 5,445,934 A | 8/1995 | Fodor et al. | |
| 5,492,806 A | 2/1996 | Drmanac et al. | |
| 5,525,464 A | 6/1996 | Drmanac et al. | |
| 5,556,752 A | 9/1996 | Lockhart et al. | |
| 5,631,734 A | 5/1997 | Stern et al. | |
| 5,695,940 A | 12/1997 | Drmanac et al. | |
| 5,700,637 A | 12/1997 | Southern | |
| 5,723,320 A | 3/1998 | Dehlinger | |
| 5,770,722 A | 6/1998 | Lockhart et al. | |
| 5,831,070 A | 11/1998 | Pease et al. | |
| 5,837,832 A | 11/1998 | Chee et al. | |
| 5,843,655 A | 12/1998 | McGall | |
| 5,856,174 A | 1/1999 | Lipshutz et al. | |
| 5,861,242 A | * 1/1999 | Chee et al. .................... | 435/5 |
| 5,872,232 A | 2/1999 | Cook et al. ................. | 536/23.1 |
| 5,919,523 A | 7/1999 | Sundberg et al. | |
| 5,986,083 A | * 11/1999 | Dwyer et al. ............... | 536/24.5 |
| 6,013,440 A | * 1/2000 | Lipshutz et al. ............... | 435/6 |
| 6,440,723 B1 | * 8/2002 | Dale ........................ | 435/287.2 |

FOREIGN PATENT DOCUMENTS

| | | |
|---|---|---|
| EP | 0 373 203 B1 | 8/1994 |
| EP | 0 742 287 A2 | 11/1996 |
| WO | WO 90/10716 | 9/1990 |
| WO | WO 93/17126 | 9/1993 |
| WO | WO 9415619 * 7/1994 | .......... A61K/31/70 |
| WO | WO 95/11995 | 5/1995 |
| WO | WO 95/35505 | 12/1995 |
| WO | 98/00564 | 1/1998 |
| WO | 98/02582 | 1/1998 |
| WO | 98/13526 | 4/1998 |
| WO | 98/39348 | 9/1998 |
| WO | 00/40525 | 7/2000 |

OTHER PUBLICATIONS

Cummins et al., "Characterization of fully 2'–modified oligonucleotide hetero–and homoduplex hybridization and nuclease sensitivity" vol. 23, pp.2019–2024, 1995.*
Moody et al.; "Regiospecific Inhibition of DNA Duplication by Antisense Phosphate–Methylated Oligodeoxynucleotides"; Nucleic Acids Research; IRL Press; vol. 17, No. 12; 1989; pp. 4769–4782.
Chalifour, Lorraine E., et al., "A Method for Analysis of Gene Expression Patterns," *Analytical Biochemistry* (1994) vol. 216:299–304.
DeRisi, Joseph L., et al., "Exploring the Metabolic and Genetic Control of Gene Expression on a Genomic Scale," *Science* (Oct. 24, 1997) vol. 278:680–686.
Ehlers, Stefan, et al., "Differentiation of T Cell Lymphokine Gene Expression: The In Vitro Acquisition of T Cell Memory," *J. Exp. Med.* (Jan. 1991) vol. 173:25–36.
Glaser, Vicki, "Rosetta Impharmatics chips in," *Nature Biotechnology* (Oct. 1997) vol. 15:937–938.
Goodwin, Raymond G., et al., "Human Interleukin 7: Molecular Cloning and Growth Factor Activity on Human and Murine B–Lineage Cells," *Proc. Nat. Acad. Sci. USA* (Jan. 1989) vol. 86:302–306.
Goodwin, Raymond G., et al., "Cloning of the Human and Murine Interleukin–7 Receptors: Demonstration of a Soluble, Form and Homology to a New Receptor Superfamily," *Cell* (Mar. 23, 1990) vol. 60:941–951.
Hoheisel, Jörg D., "Oligomer–chip Technology," *TibTech* (Nov. 1997) vol. 15:465–469.
Leonard, Warren J., et al., "Molecular Cloning and Expression of cDNAs for the Human Interleukin–2 Receptor," *Nature* (Oct. 1984) vol. 311:626–631.
Lockhart, David J., et al., "Epression Monitoring by Hybridization in High–Density Oligonucleotide Arrays," *Nature Biotechnology* (Dec. 1996) vol. 14: 1675–1680.
Marshall, Andrew, et al., "DNA Chips: An Array of Possibilities," *Nature Biotechnology* (Jan. 1998) vol. 16:27–31.
Nguyen, Catherine, et al., "Differential Gene Expression in the Murine Thymus Assayed by Quantitative Hybridization of Arrayed cDNA Clones," *Genomics* (1995) vol. 29:207–216.

(List continued on next page.)

*Primary Examiner*—Marianne P. Allen
(74) *Attorney, Agent, or Firm*—Albert P. Halluin; Eric Witt; Wilson Sonsini Goodrich & Rosati

(57) ABSTRACT

The present invention provides methods for producing arrays having associated modified nucleic acid structures, e.g. acid stable and/or end-blocked nucleic acids such as 2'-O—R oligonucleotides. In one embodiment, arrays produced using the methods of the invention exhibit an increased binding affinity with complementary nucleic acids, and in particular with complementary RNA. In another embodiment, the associated nucleic acids of the array produced using the methods of the invention exhibit substantial acid resistance, allowing the arrays to be treated with low pH solutions. In another embodiment, the modified associated nucleic acids of the array produced using the methods of the invention exhibit substantial resistance to nuclease degradation.

12 Claims, 10 Drawing Sheets

OTHER PUBLICATIONS

Nishi, Tatsunari et al., "Cloning and Expression of a Novel Variant of Human Interferon-γ cDNA," *J. Biochem* (1985) vol. 97:153–159.

Ramsay, Graham, "DNA Chips: State of the Art," *Nature Biotechnology* (Jan. 1998) vol. 16:40–44.

Schena, Mark, et al., "Parallel Human Genome Analysis: Microarray–Based Expression Monitoring of 1000 Genes," *Proc. Natl. Acad. Sci. USA* (Oct. 1996) vol. 93:10614–10619.

Shalon, Dari, et al., "A DNA Microarray System for Analyzing Complex DNA Samples Using Two–Color Fluorescent Probe Hybridization," *Genome Research* (1996) vol. 6:639–645.

Zhao, Nanding, et al., "High–Density cDNA Filter Analysis: A Novel Approach for Large–Scale, Quantitative Analysis of Gene Expression," *Gene* (1995) vol. 156:207–213.

\* cited by examiner

ACID STABLE

ACID STABLE, END-BLOCKED

5' end
Butanol Blocking Group

Nuclease Resistant

1' modification
Nuclease Resistant

Substitution in O of sugar group
Nuclease Resistant
Higher $T_m$s

Phosphoramidate
Nuclease Resistant
Higher $T_m$s

US 6,844,151 B1

METHODS FOR PRODUCTION OF ARRAYS WITH MODIFIED OLIGONUCLEOTIDE AND POLYNUCLEOTIDE COMPOSITIONS

FIELD OF THE INVENTION

The field of this invention is arrays having associated oligonucleotides and/or polynucleotides, methods of producing such arrays, and uses thereof.

BACKGROUND OF THE INVENTION

Arrays of binding agents, such as oligonucleotides and polynucleotides, have become an increasingly important tool in the biotechnology industry and related fields. These arrays, in which a plurality of binding agents are deposited onto a solid support surface in the form of an array or pattern, find use in a variety of applications, including drug screening, nucleic acid sequencing, mutation analysis, and the like. One important use of arrays is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared.

In methods of differential gene expression, arrays find use by serving as a substrate with associated binding fragments such as oligonucleotides. Nucleic acid sequences are obtained from analogous cells, tissues or organs of a healthy and diseased organism, and hybridized to the immobilized set of binding fragments associated with the array. Differences between the resultant hybridization patterns are then detected and related to differences in gene expression in the two sources.

A variety of different array technologies have been developed in order to meet the growing need of the biotechnology industry. Despite the wide variety of array technologies currently in preparation or available on the market, there is a continued need to identify new array devices to meet the needs of specific applications. Of particular interest are arrays which provide increased binding affinity, because these allow the use of shorter binding fragments and fewer bound fragments can be used to obtain the results currently available with conventional technology. Also of interest is the development of an array capable of providing high throughput analysis of differential gene expressions where the array itself is reusable. Such an array is needed for a number of reasons such as decreasing experimental variability, confirming results, and for decreasing costs of such analysis.

SUMMARY OF THE INVENTION

The present invention provides methods of producing arrays having associated oligonucleotide and/or polynucleotides with modified structures (e.g., 1', 2', 3', 5' modifications, modifications to the ribose oxygen, and 2'-substitutions), methods of making such arrays, assays for using such arrays, and kits containing such arrays. The modifications described herein provide numerous advantages, including a higher binding affinity for complementary nucleic acids, acid resistance, and/or nuclease resistance. The invention comprises an array device comprised of a support surface and polymer molecules bound to the support surface. The polymer molecules are not naturally occurring oligonucleotides or polynucleotides, but rather have modified backbones with bases attached in the desired sequential positioning and the desired spacing between the bases. The backbone is preferably modified to obtain improved results compared to natural oligonucleotides or polynucleotides including (1) higher binding affinity; (2) greater acid resistance; (3) greater resistance to enzymatic degradation; and/or (4) overall better performance and reusability.

In one embodiment, the modified associated oligonucleotides and/or polynucleotides of the invention provide additional binding affinity with respect to corresponding, unmodified oligonucleotides having the same sequence. The binding affinity is preferably increased by a modification at the 2' site of the sugar group, e.g., a 2'-F or a 2'-OR modification such as 2'-methyl or 2'-O-methoxyethoxy. Alternatively or in combination, the binding affinity can be increased by modification in the 3' linkage group, e.g., phosphoramidate linkages, or a modification replacing the oxygen with a carbon. In yet another embodiment, the modified associated oligonucleotides and/or polynucleotides are characterized by modification of at least 25% of the internucleoside linkages of the oligonucleotide and/or polynucleotide.

In another embodiment, the modified associated oligonucleotides and/or polynucleotides of the array exhibit substantial acid resistance, allowing the arrays to be treated with low pH solutions. This allows the array to be exposed to low pH in order to remove any bound nucleic acids that are not modified, e.g., bound test nucleic acids. In yet another embodiment, the modified oligonucleotides and/or polynucleotides of the array have a pH stability of at least one hour at 37° C. at a pH range of about 0.5 to about 10 including across the pH range of about 0.5 to 6.0.

It is thus an object of the present invention to provide arrays having associated chemically modified oligonucleotides and/or polynucleotides characterized by substantial acid resistance. Such arrays may be exposed to low pH environments to facilitate clearance from the array of the test binding agents.

In yet another embodiment, the modified associated oligonucleotides and/or polynucleotides of the array exhibit substantial resistance to nuclease degradation. These molecules preferably have an end-blocking group that confers nuclease resistance to the molecule, e.g., a butanol or butyl group.

It is thus an object of the invention to provide arrays having associated chemically modified oligonucleotides and/or polynucleotides to confer substantial nuclease resistance. Nucleases can be used to digest the test substrate binding agent, freeing the associated binding agents for further use. The chemical modification may be on the 5' end for oligonucleotides and/or polynucleotides attached to a substrate at the 3' end, or alternatively the chemical modification may be on the 3' end for oligonucleotides and/or polynucleotides attached to a substrate at the 5' end. The associated oligonucleotides and/or polynucleotides remain unaffected as to the binding capacity of the associated oligonucleotides.

These arrays also offer the significant advantage that the individual chip can be tested for efficacy and/or quality prior to use with a test sample, which is particularly helpful if the amount of test sample is limited or if the array is being used as a medical device and must comply with FDA quality control requirements.

The present invention further provides an assay using the arrays of the invention to determine physiological responses such as gene expression, where the response is determined by the hybridization pattern of the array after exposure to test samples. The test samples may be mRNA, cDNA, whole cell extracts, and the like.

It is an advantage of the associated modified oligonucleotides and/or polynucleotides of the arrays of the invention that the chemical modifications enhance the chemical binding interactions, e.g., increase binding affinity over standard Watson-Crick base pairing with complementary oligonucleotides and/or polynucleotides, particularly when binding to mRNA.

It is another advantage that the modified oligonucleotides and/or polynucleotides of the array may be synthesized to have approximately the same $T_m$, by varying the length of the nucleic acids in each composition.

It is another advantage that modified oligonucleotides and/or polynucleotides of the invention hybridize more tightly with complementary RNA sequences than natural DNA oligonucleotides, allowing the use of shorter binding fragments (e.g. one or more oligonucleotides in lieu of a complete cDNA).

It is an advantage of the associated modified oligonucleotides and/or polynucleotides of the invention that the acid stable modifications confer an improved stability on the modified oligonucleotides and/or polynucleotides in an acidic environment (e.g., as low as pH of 1 to 2).

It is another advantage of the associated oligonucleotides and/or polynucleotides of the invention that they bind with specificity to test nucleic acids.

It is an object of the invention that the oligonucleotides and/or polynucleotides can be used in a variety of array applications, such as identification of new genes, determination of expression levels, diagnosis of disease, and the like.

These and other objects, advantages, and features of the invention will become apparent to those skilled in the art upon reading the details of the oligonucleotides and/or polynucleotides and uses thereof as more fully described below.

DETAILED DESCRIPTION OF THE PREFERRED EMBODIMENTS

Figure 1:
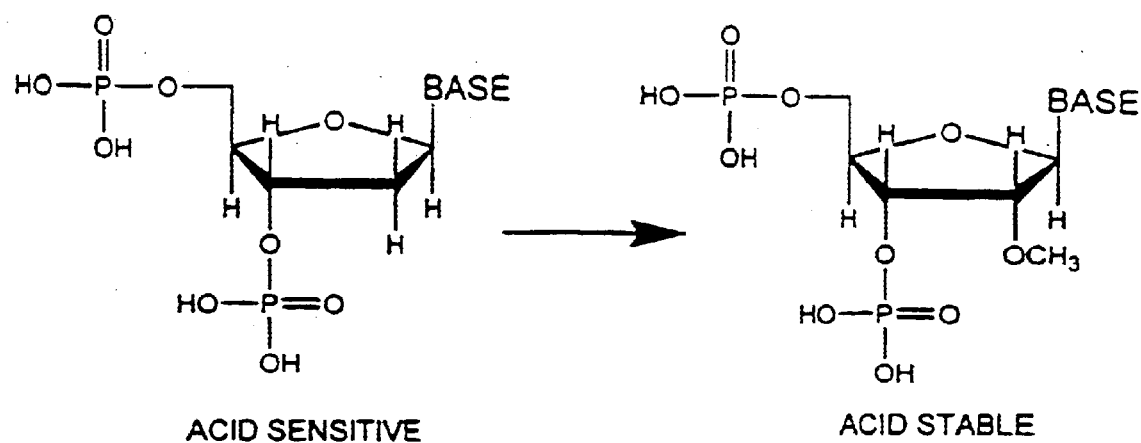
FIGS. 1–7 illustrate the chemical structure of exemplary modifications that result in acid stability.
Figure 2:
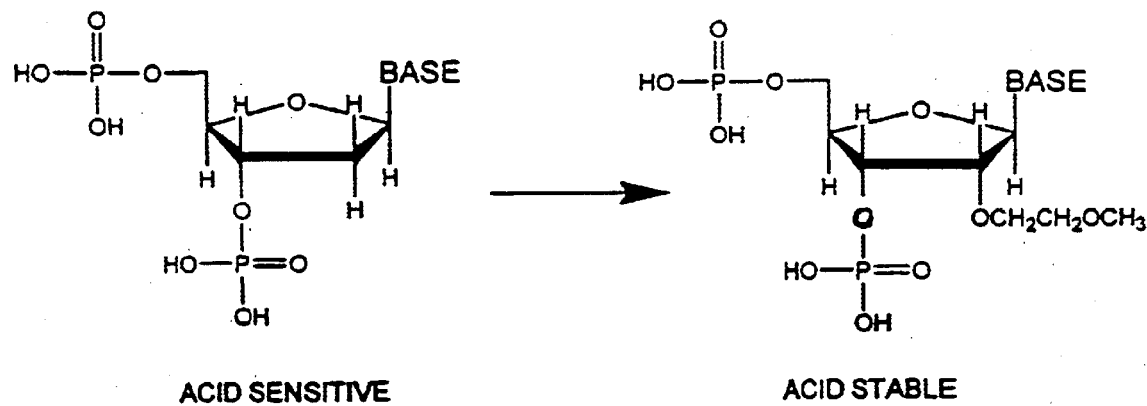
Figure 3:
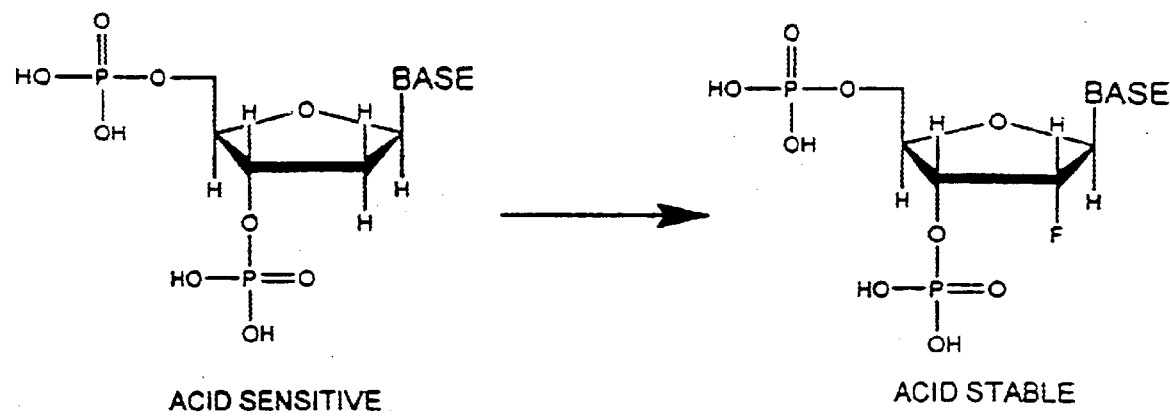
Figure 4:
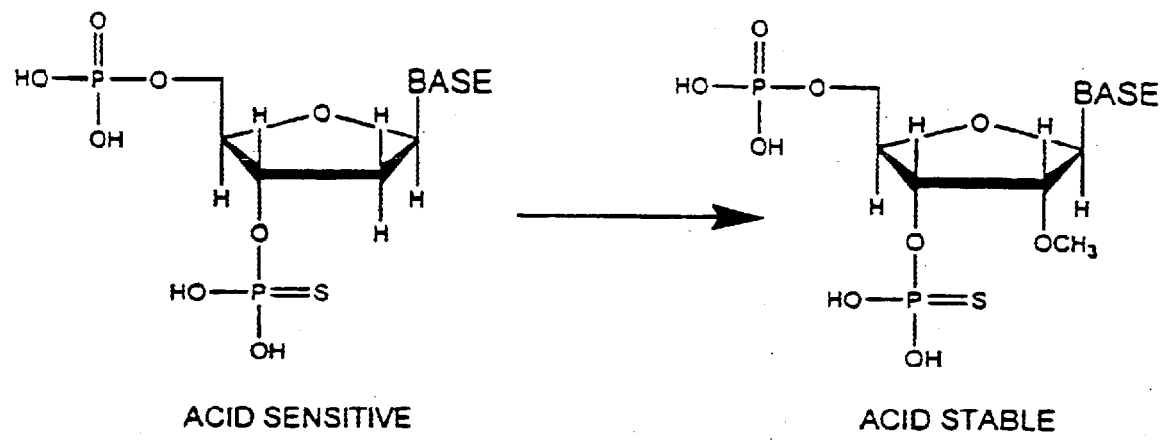
Figure 5:
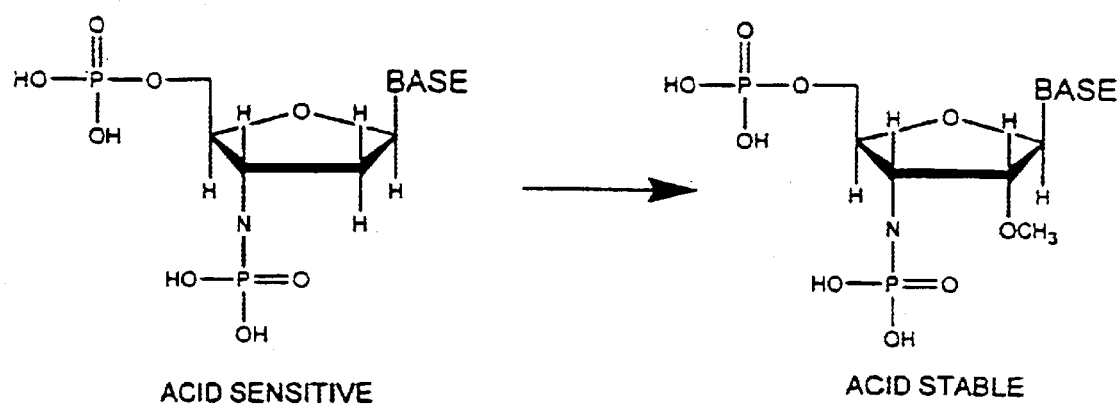
Figure 6:
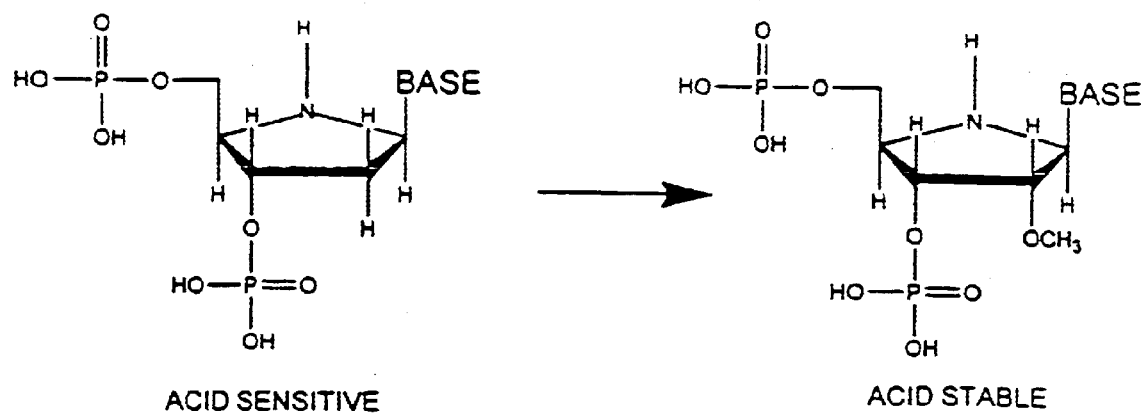

It is to be understood that this invention is not limited to the particular methodology, support surfaces, materials and modifications described and as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an oligonucleotide" may include a plurality of oligonucleotide molecules and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned are incorporated herein by reference for the purpose of describing and disclosing, for example, materials, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

DEFINITIONS

The terms "nucleic acid" and "nucleic acid molecule" as used interchangeably herein, refer to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The term "oligonucleotide" as used herein refers to a nucleic acid molecule comprising from about 2 to about 300 nucleotides. Oligonucleotides for use in the present invention are preferably from 80–200, more preferably from about 100–200, and even more preferably from about 100–150 nucleotides in length.

The term "polynucleotide" as used herein refers to nucleic acid molecules comprising a plurality of nucleotide monomers including but not limited to nucleic acid molecules comprising over 200 nucleotides.

The terms "modified oligonucleotide" and "modified polynucleotide" as used herein refers to oligonucleotides and/or polynucleotides with one or more chemical modifications at the molecular level of the natural molecular structures of all or any of the bases, sugar moieties, internucleoside phosphate linkages, as well as to molecules having added substituents, such as diamines, cholesterol or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3',5'-2' or 5'-5' linkages, and combinations of such similar linkages (to produce mixed backbone modified oligonucleotides). The modifications can be internal (single or repeated) or at the end(s) of the oligonucleotide molecule, and can include additions to the molecule of the internucleoside phosphate linkages, such as cholesteryl, diamine compounds with varying numbers of carbon residues between amino groups and terminal ribose, and deoxyribose and phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an oligomer could covalently attach to the 5' end of an mRNA or to another electrophilic site. The terms "modified oligonucleotides" and "modified polynucleotides" also include oligonucleotides and/or polynucleotides comprising modifications to the sugar moieties (e.g., 2'-substituted ribonucleotides or deoxyribonucleotide monomers), any of which are connected together via 5' to 3' linkages. Modified oligonucleotides may also be comprised of PNA or morpholino modified, backbones where target specificity of the sequence is maintained. A modified oligonucleotide of the invention (1) does not have the structure of a naturally occurring oligonucleotide and (2) will hybridize to a natural oligonucleotide mRNA, or cDNA. Further, the modification preferably provides (3) higher binding affinity, (4) greater acid resistance, and (5) better stability against digestion with enzymes as compared to a natural oligonucleotide.

The term "oligonucleotide backbone" as used herein refers to the structure of the chemical moiety linking nucleotides in a molecule. The invention preferably comprises a backbone which is different from a naturally occurring backbone and is further characterized by (1) holding bases in correct sequential order and (2) holding bases a correct distance between each other to allow a natural oligonucleotide to hybridize to it. This may include structures formed from any and all means of chemically linking nucleotides. A modified backbone as used herein includes modifications (relative to natural linkages) to the chemical linkage between nucleotides, as well as other modifications that may be used to enhance stability and affinity, such as modifications to the sugar structure. For example an α-anomer of deoxyribose may be used, where the base is inverted with respect to the natural β-anomer. In a preferred embodiment, the 2'-H or 2'-OH of the sugar group (for RNA and DNA, respectively) may be altered to 2'-O-alkyl or 2'-O-alkyl-n (O-alkyl), which provides resistance to degradation without comprising affinity.

The term "end-blocked" as used herein refers to an oligonucleotide with a chemical modification at the molecular level that prevents the degradation of selected nucleotides, e.g., by nuclease action. This chemical modification is positioned such that it protects the integral portion of the oligonucleotide, for example the region of the oligonucleotide that is targeted for hybridization (i.e., the test sequence of the oligonucleotide). An end block may be a 3' end block or a 5' end block. For example, a 3' end block may be at the 3'-most position of the molecule, or it may be internal to the 3' ends, provided it is 3' of the integral sequences of the oligonucleotide.

The term "substantially nuclease resistant" refers to oligonucleotides that are resistant to nuclease degradation as compared to naturally occurring or unmodified oligonucleotides. Modified oligonucleotides of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant oligonucleotides include, but are not limited to, oligonucleotides with modified backbones such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n (O-alkyl), 3'-O-alkyls, 3'-O-alkyl-n(O-alkyl), 3'-O-methyl ribonucleotides, 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to oligonucleotides that are resistant to acid degradation as compared to unmodified oligonucleotides. Typically, the relative acid resistance of an oligonucleotide will be measured by comparing the percent degradation of a resistant oligonucleotide with the percent degradation of its unmodified counterpart (i.e., a corresponding oligonucleotide with "normal" backbone, bases, and phosphodiester linkages). An oligonucleotide that is acid resistant is preferably at least 1.5 times more resistant to acid degradation, at least 2 times more resistant, even more preferably at least 5 times more resistant, and most preferably at least 10 times more resistant than their unmodified counterpart.

The term "alkyl" as used herein refers to a branched or unbranched saturated hyrdrocarbon chain containing 1–6 carbon atoms, such as methyl, ethyl, propyl, tert-butyl, n-hexyl and the like.

The term "array type" refers to the type of gene represented on the array by the associated test oligonucleotides, where the type of gene that is represented on the array is dependent on the intended purpose of the array, e.g., to monitor expression of key human genes, to monitor expression of known oncogenes, etc., i.e., the use for which the array is designed. As such, all of the test oligonucleotides on a given array correspond to the same type or category or group of genes. Genes are considered to be of the same type if they share some common linking characteristics, such as: species of origin, e.g., human, mouse, rat, etc.; tissue or cell type of origin, e.g., muscle, neural, dermal, organ, etc.; disease state, e.g., cancer; functions, e.g., protein kinases, tumor supressors and the like; participation in the same normal biological process, e.g., apoptosis, signal transduction, cell cycle regulation, proliferation, differentiation etc.; and the like. For example, one array type is a "cancer array" in which each of the "unique" associated test oligonucleotides correspond to a gene associated with a cancer disease state. Likewise, a "human array" may be an array of test oligonucleotides corresponding to unique tightly regulated human genes. Similarly, an "apoptosis array" may be an array type in which the associated test oligonucleotides correspond to unique genes associated with apoptosis.

The terms "associated oligonucleotide," "associated polynucleotide" and "substrate oligonucleotide" and the like refer to the oligonucleotide or polynucleotide composition that makes up each of the samples associated to the array. Thus, the term "associated oligonucleotide" includes oligonucleotide compositions of unique sequences and/or control or calibrating sequences (e.g., oligonucleotides corresponding to housekeeping genes). The oligonucleotide and/or polynucleotide compositions are preferably comprised of single stranded nucleic acid, where all of the nucleic acids in a sample composition may be identical to each other. Alternatively, there may be nucleic acids having two or more sequences in each composition, for example two different oligonucleotides that are separate but complementary to each other.

THE INVENTION IN GENERAL

Arrays having associated oligonucleotides and/or polynucleotides with modified backbone structures, such as oligonucleotides with 2'-O-alkyl and 2'-O-alkyl-n(O-alkyl) sugar moieties, changes in the ribose oxygen, 5' linkage modifications, and/or 3' linkage modifications, are provided. Modified oligonucleotides and polynucleotides of the invention also may be acid resistant and/or exonuclease resistant to further decrease the sensitivity of the oligonucleotide molecule. In one embodiment, an exonuclease resistant block is added to the 3' or the 5' end of the oligonucleotide or polynucleotide depending on the attachment of the nucleic acid to the substrate. The resulting modified oligonucleotides and/or polynucleotides of the invention bind tightly to their RNA or DNA targets.

Modified oligonucleotides and/or polynucleotides of the invention preferably have an increased binding affinity over their non-modified RNA or DNA counterparts. This binding affinity can be determined using $T_m$ assays such as those described in L. L. Cummins et al. *Nucleic Acids Research* 23:2019–2024 (1995). Typically, the $T_m$ of an oligonucleotide binding to RNA will increase approximately 1° C. for each 2'-O-methyl substitution in a molecule, and the $T_m$ increases even more for 2'-O-propyl and 2'-F substitutions. Thus, in one embodiment, the $T_m$ of the modified oligonucleotide bound to RNA is 2–15° C., and even more preferably 8–10° C. higher than the corresponding non-modified DNA oligonucleotide.

The modified oligonucleotides and/or polynucleotides of the array may be synthesized to have approximately the same $T_m$, by varying the length of the nucleic acids in each composition. Thus, an oligonucleotide with an A-T rich sequence would be designed to be longer than an oligonucleotide with a G-C rich sequence to provide approximately the same $T_m$. The $T_m$ of each of the compositions on an array can be held relatively constant by providing lengths of oligonucleotides and polynucleotides based on the binding affinity of the base sequence.

Acid stable associated oligonucleotides and/or polynucleotides of the invention are stable when exposed to a pH of 1–2, while their binding partners are not. This allows an array having associated acid stable oligonucleotides and/or polynucleotides to be exposed to a first sample, treated with an acidic solution applied in any of several possible protocols to free the array from the first binding partner, and reused with a second sample. Direct comparison of two different samples of binding partners using a single array has the advantage of limiting potential experimental variation present when comparing multiple arrays. Performing the experiment with the same sample on the same array allows a confirmation of the results obtained in the first instance, thus effectively confirming results without having variation in the array composition.

Similarly, associated end-blocked oligonucleotides and/or polynucleotides display a resistance to nucleases, allowing the arrays to be exposed to DNA nucleases to free the array from a sample of binding partners. An array of the invention having nuclease resistant associated oligonucleotides can be treated with an appropriate nuclease and reused with a different or the same sample.

The arrays of the present invention encompass associated oligonucleotides chemically modified to be acid stable from a pH of 0.01 to 7.0, and more preferably acid stable in a pH of 1.0 to 4.0, allowing such molecules to retain their structural integrities in acidic environments. Although any 2'-modified oligonucleotide may be used in the present invention, in a preferred embodiment the oligonucleotides of the invention are 2'-O-alkyl and 2'-O-alkyl-n(O-alkyl) oligonucleotides which, unlike unsubstituted phosphodiester or phosphorothioate DNA or RNA, exhibit significant acid resistance in solutions with pH as low as 0–1 even at 37° C. Acid stability of this first component coupled with the introduction of 3' and/or 5' acid stable, exonuclease resistant ends, confers several unique properties on 2'-O-alkyl and 2'-O-alkyl-n(O-alkyl) oligonucleotides. These low toxicity, highly specific, acid stable, end-blocked 2'-O-alkyl and 2'-O-alkyl-n(O-alkyl) oligonucleotides represent a novel and improved oligonucleotide structure for use in array technologies.

Typically, the relative nuclease resistance of a oligonucleotide can be measured by comparing the percent digestion of a resistant oligonucleotide with the percent digestion of its unmodified counterpart (i.e., a corresponding oligonucleotide with "normal" backbone, bases, and phosphodiester linkage). Percent degradation may be determined by using analytical HPLC to assess the loss of full length oligonucleotides, or by any other suitable methods (e.g., by visualizing the products on a sequencing gel using staining, autoradiography, fluorescence, etc., or measuring a shift in optical density). Degradation is generally measured as a function of time.

Comparison between unmodified and modified oligonucleotides can be made by ratioing the percentage of intact modified oligonucleotide to the percentage of intact unmodified oligonucleotide. For example, if, after 15 minutes of exposure to a nuclease, 25% (i.e., 75% degraded) of an unmodified oligonucleotide is intact, and 50% (i.e., 50% degraded) of a modified oligonucleotide is intact, the modified oligonucleotide is said to be 2 times (50% divided by 25%) more resistant to nuclease degradation than is the unmodified oligonucleotide. Generally, a substantially nuclease resistant oligonucleotide will be at least about 1.25 times more resistant to nuclease degradation than an unmodified oligonucleotide with a corresponding sequence, typically at least about 1.5 times more resistant, preferably about 1.75 times more resistant, and more preferably at least about 10 times more resistant after 15 minutes of nuclease exposure.

Percent acid degradation may be determined by using analytical HPLC to assess the loss of full length oligonucleotides, or by any other suitable methods (e.g. by visualizing the products on a sequencing gel using staining, autoradiography, fluorescence, etc., or measuring a shift in optical density). Degradation is generally measured as a function of time.

Comparison between unmodified and modified oligonucleotides can be made by ratioing the percentage of intact modified oligonucleotide to the percentage of intact unmodified oligonucleotide. For example, if, after 30 minutes of exposure to a low pH environment, 25% (i.e., 75% degraded) of an unmodified oligonucleotide is intact, and 50% (i.e., 50% degraded) of a modified oligonucleotide is intact, the modified oligonucleotide is said to be 2 times (500% divided by 25%) more resistant to nuclease degradation than is the unmodified oligonucleotide. Generally, substantially "acid resistant" oligonucleotides will be at least about 1.25 times more resistant to acid degradation than an unmodified oligonucleotide with a corresponding sequence, typically at least about 1.5 times more resistant, preferably about 1.75 more resistant, more preferably at least times more resistant and even more preferably at least about 10 times more resistant after 30 minutes of exposure at 37° C. to a pH of about 1.5 to about 4.5.

In a preferred embodiment, the end-blocked oligonucleotides of the compositions and methods of the invention are substantially nuclease resistant, substantially acid resistant, and preferably, both substantially nuclease resistant and substantially acid resistant. This embodiment includes oligonucleotides completely or partially derivatized by one or more linkages from the group comprised of phosphorothioate linkages, 2'-O-methyl-phosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, p-isopropyl oligonucleotides, phosphodiester, 2'-O($CH_2CH_2O)_xCH_3$, butyne, phosphotriester, phosphoramidate, propargyl, siloxane, carbonate, carboxymethylester, methoxyethoxy, acetamidate, carbamate, thioether, bridged phosphoramidate, bridged methylene phosphonate, methylphosphonate, phosphorodithioate, bridged phosphorothioate and/or sulfone internucleotide linkages, or 3'-3' or 5'-5' or 5'-2' linkages, and combinations of such similar linkages (to produce mixed backbone modified oligonucleotides), and any other backbone modifications.

Figure 7:
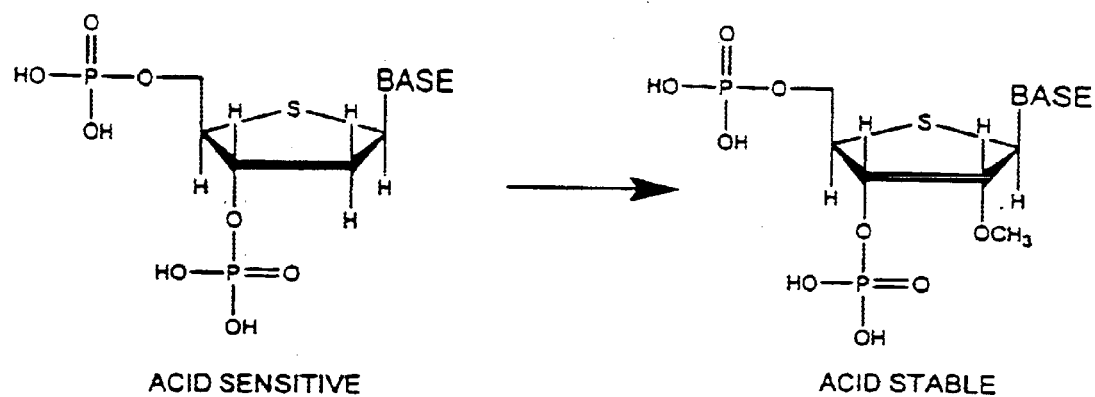
Figure 8:
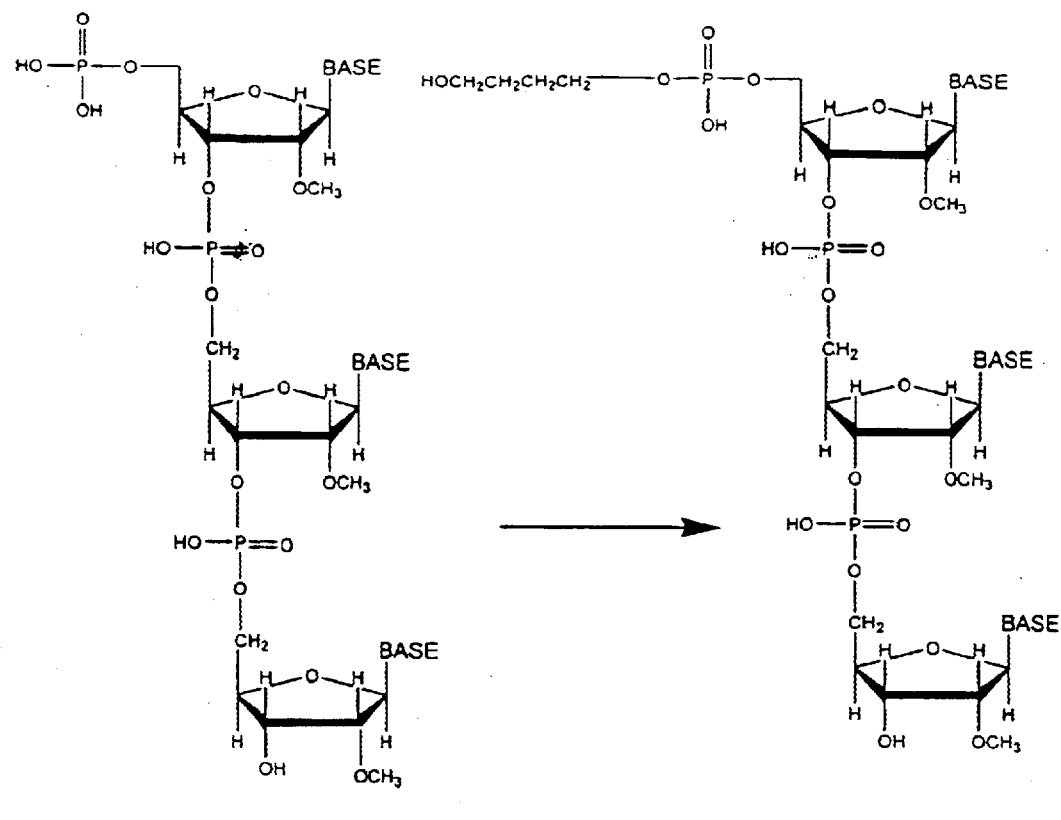
FIGS. 8–9 illustrate the chemical structure of end-blocked, acid stable molecules used in the invention.
Figure 9:
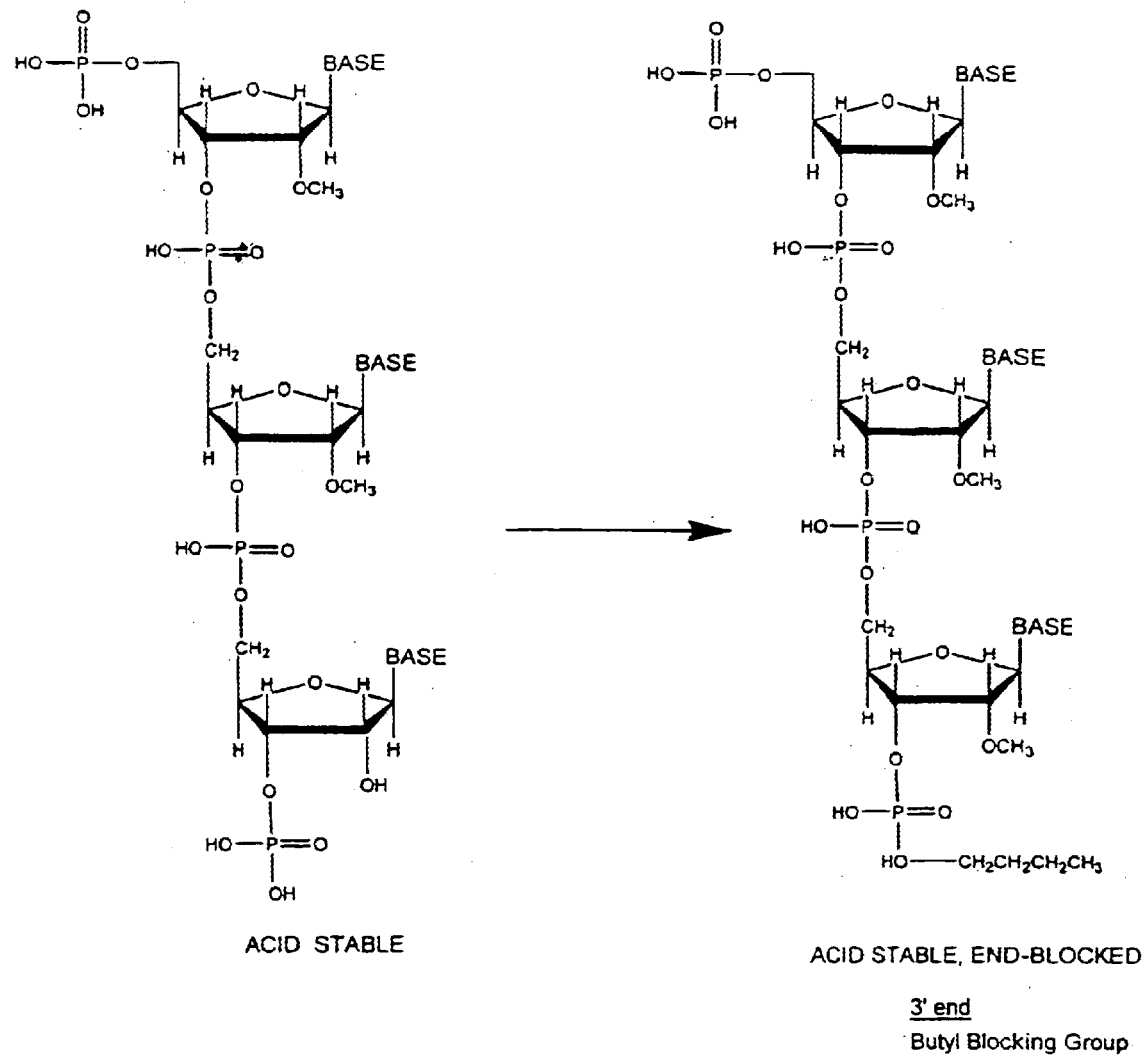
Figure 10:
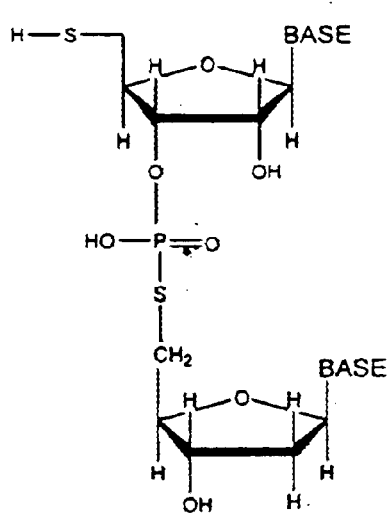
FIG. 10 illustrates other potential modifications that may be used in the present invention.
Figure 10:
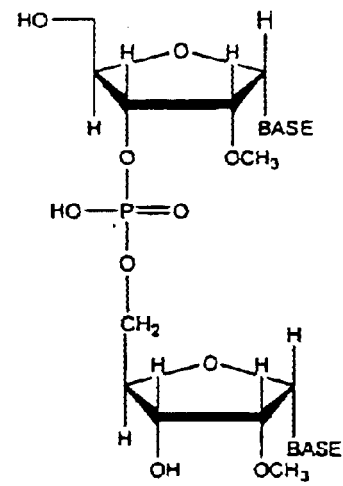
Figure 10:
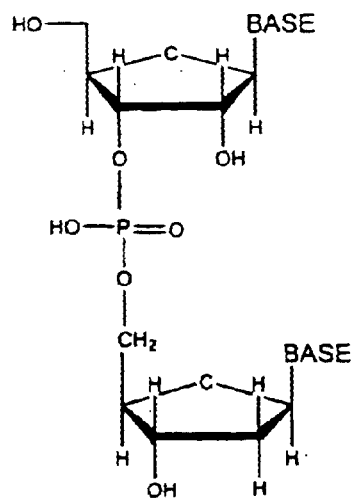
Figure 10:
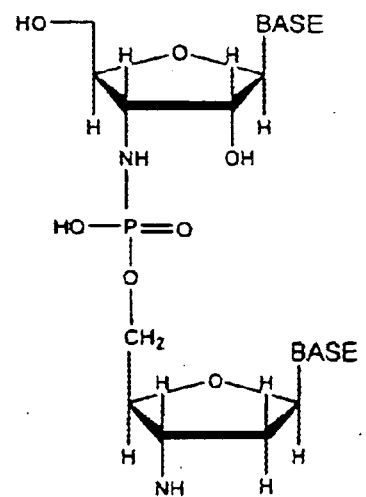

Exemplary modifications that result in acid stability can be seen in FIGS. 1–6. End-blocked acid stable molecules are illustrated in FIGS. 7–8. Other modifications that may be of use in the present invention are illustrated. See "The Medicinal Chemistry of Oligonucleotides" in *Medical Intelligence Unit: Therapeutic Applications of Oligonucleotides* (1995) pp. 85–108; and Mesmaeker et al., *Acc. Chem. Res.*, 28:366–374 (1995).

This embodiment also includes other modifications that render the oligonucleotides and/or polynucleotides substantially resistant to nuclease activity. Methods of rendering an oligonucleotide nuclease resistant include, but are not limited to, covalently modifying the purine or pyrimidine bases that comprise the oligonucleotide. For example, bases may be methylated, hydroxymethylated, or otherwise substituted (e.g., glycosylated) such that the oligonucleotides comprising the modified bases are rendered substantially nuclease resistant.

In a preferred embodiment, the oligonucleotide and/or polynucleotide will have a backbone substantially resistant to acid degradation, exonuclease digestion, and endonuclease digestion. In the most preferred embodiment an oligonucleotide is uniformly modified with 2'-O-alkyl or 2'-O-alkyl-n(O-alkyl) groups, i.e., every base of the oligonucleotide is a 2'-O-alkyl or 2'-O-alkyl-n(O-alkyl) modified base.

In another embodiment, the associated oligonucleotides and/or polynucleotides of the current invention are used for diagnostic purposes. For example, oligonucleotides of the current invention may be used to detect complementary oligonucleotides by contacting an oligonucleotide of the invention with an oligonucleotide sample under conditions that allow for the hybridization of the oligonucleotide of the invention to any complementary oligonucleotide present in the sample, and detecting such hybridization.

Oligonucleotides with a range of nuclease-resistant backbones were evaluated. As a result, a preferred embodiment of the present invention is an end-blocked oligonucleotide with the chemical backbone structure of 5'-butanol-2'-O-alkyl RNA-butanol-3' or 2'-O-alkyl-O-alkyl. A particularly preferred embodiment of the present invention is an oligonucleotide with the chemical backbone structure of 5'-butanol-2'-O-methyl RNA-butanol-3',5'-butanol-2'-O-alkyl-O-alkyl RNA-butanol-3' or 2'-O-alkyl-O-alkyl RNA. The end-blocking group on one end of the oligonucleotide may not be needed, depending on the manner of association with the substrate, as will be apparent to one skilled in the art upon reading the present disclosure.

ASSOCIATED OLIGONUCLEOTIDE AND POLYNUCLEOTIDE COMPOSITIONS OF THE ARRAYS

Each associated oligonucleotide and/or polynucleotide composition of the pattern present on the surface of the substrate is preferably made up of a set of unique nucleic acids, and preferably a unique oligonucleotide composition. By "unique composition" is meant a collection or population of single stranded oligonucleotides capable of participating in a hybridization event under appropriate hybridization conditions, where each of the individual oligonucleotides may be the same—have the same nucleotide sequence—or different sequences, for example the oligonucleotide composition may consist of two different oligonucleotides that are complementary to each other (i.e., the two different oligonucleotides are complementary but physically separated so as to be single stranded, i.e., not hybridized to each other). In many embodiments, the oligonucleotide compositions will comprise two complementary, single stranded oligonucleotides.

In those compositions having unique oligonucleotides, the sequence of the oligonucleotides are chosen in view of the type and the intended use of the array on which they are present. The unique oligonucleotides are preferably chosen so that each distinct unique oligonucleotide does not cross-hybridize with any other distinct unique oligonucleotide on the array, i.e., the oligonucleotide will not cross-hybridize to any other oligonucleotide compositions that correspond to a different gene falling within the broad category or type of genes represented on the array under appropriate conditions. As such, the nucleotide sequence of each unique oligonucleotide of a composition will have less than 90% homology, usually less than 85% homology, and more usually less than 80% homology with any other different associated oligonucleotide composition of the array, where homology is determined by sequence analysis comparison using the FASTA program using default settings. The sequence of unique associated oligonucleotides in the compositions are not conserved sequences found in a number of different genes (at least two), where a conserved sequence is defined as a stretch of from about 4 to about 80 nucleotides which have at least about 90% sequence identity, where sequence identity is measured as above. The associated oligonucleotide will generally have a length of from about 80 to about 300 nucleotides, usually from 100 to about 200 nucleotides. The length of the nucleic acid can be chosen to best provide binding to the test sequence.

Although in a preferred embodiment the associated modified oligonucleotide composition will not cross-hybridize with any other associated oligonucleotides on the array under standard hybridization conditions, associated oligonucleotides and hybridization conditions can be altered to allow binding to multiple associated oligonucleotide compositions. For example, in determining the relatedness of a sample to oligonucleotides representing different members of a class of proteins, the oligonucleotide sequences may be more similar and/or less stringent hybridization conditions may be used.

CHEMICAL MODIFICATIONS OF OLIGONUCLEOTIDES AND/OR POLYNUCLEOTIDES OF THE INVENTION

The oligonucleotides and/or polynucleotides of the invention may contain any modification that confers on the molecules greater binding with other nucleic acids, that increases the acid stability and/or increases the nuclease stability of the molecule. This includes oligonucleotides and/or polynucleotides completely derivatized by phosphorothioate linkages, 2'-O-methylphosphodiesters, 2'-O-alkyl, 2'-O-alkyl-n(O-alkyl), 2'-fluoro, 2'-deoxy-erythropentofuranosyl, 3'-O-methylphosphodiesters, p-ethoxy oligonucleotides, pisopropyl oligonucleotides, phosphoramidates, phosphoroamidites, chimeric linkages, carbonates, amines, formacetals, silyls and siloxys, sulfonates, hydrocarbon, amides, ureas and any other backbone modifications, as well as other modifications, which render the oligonucleotides and/or polynucleotides substantially resistant to endogenous nuclease activity. The nucleotides in each oligonucleotide and/or polynucleotide may each contain the same modifications, may contain combinations of these modifications, or may combine these modifications with phosphodiester linkages. Additional methods of rendering oligonucleotides and/or polynucleotides nuclease resistant include, but are not limited to, covalently modifying the purine or pyrimidine bases that comprise the oligonucleotide. For example, bases may be methylated, hydroxymethylated, or otherwise substituted (e.g., glycosylated) such that the oligonucleotides and/or polynucleotides comprising the modified bases are rendered substantially acid and nuclease resistant.

The ring structure of the ribose group of the nucleotides in the modified oligonucleotide and/or polynucleotide may also have an oxygen in the ring structure substituted with N—H, N—R, S and/or methylene.

Although 2'-O-alkyl substituted oligonucleotides and/or polynucleotides exhibit marked acid stability and endonuclease resistance, they are sensitive to 3' exonucleases. In order to enhance the exonuclease resistance of 2'-O-alkyl substituted oligonucleotides and/or polynucleotides, the 3' or 5' and 3' ends of the ribooligonucleotide sequence are preferably attached to an exonuclease blocking function. For example, one or more phosphorothioate nucleotides can be placed at either end of the oligoiibonucleotide. Additionally, one or more inverted bases can be placed on either end of the oligoribonucleotide, or one or more alkyls, e.g., butanol-substituted nucleotides or chemical groups, can be placed on one or more ends of the oligoribonucleotide. Accordingly, a preferred embodiment of the present invention is an oligonucleotide comprising a oligonucleotide having the following structure:

A-B-C wherein "B" is a 2'-O-alkyl or 2'-O-alkyl-n(O-alkyl) oligoribonucleotide between about 2 and about 300 bases in length, and "A" and "C" are respective 5' and 3' end blocking groups (e.g., one or more phosphorothioate nucleotides (but typically fewer than six), inverted base linkages, or alkyl, alkenyl, or alkynl groups or substituted nucleotides or 2'-O-alkyl-n(O-alkyl)). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure OH—$CH_2CH_2CH_2CH_2$ (4-hydroxybutyl) which is also referred to as a C4 spacer.

OLIGONUCLEOTIDE AND POLYNUCLEOTIDE SYNTHESIS

Oligonucleotides can be synthesized on commercially purchased DNA synthesizers from <1 uM to >1 mM scales using standard phosphoramidite chemistry and methods that are well known in the art, such as, for example, those disclosed in Stec et al., *J. Am. Chem. Soc.* 106:6077–6089 (1984), Stec et al., *J. Org. Chem.* 50(20):3908–3913 (1985), Stec et al., *J. Chromatog.* 326:263–280 (1985), LaPlanche et al., *Nuc. Acid. Res.* 14(22):9081–9093 (1986), and Fasman, *Practical Handbook of Biochemistry and Molecular Biology*, 1989, CRC Press, Boca Raton, Fla., herein incorporated by reference.

Oligonucleotides can be deprotected following phosphoramidite manufacturer's protocols. Unpurified oligonucleotides may be dried down under vacuum or precipitated and then dried. Sodium salts of oligonucleotides can be prepared using the commercially available DNA-Mate (Barkosigan Inc.) reagents or conventional techniques such as a commercially available exchange resin, e.g., Dowex, or by addition of sodium salts followed by precipitation, diafiltration, or gel filtration, etc.

Oligonucleotides to be purified can be chromatographed on commercially available reverse phase or ion exchange media, e.g., Waters Protein Pak, Pharmacia's Source Q, etc. Peak fractions can be combined and the samples desalted and concentrated by means of reverse phase chromatography on poly(styrene-divinylbenzene) based columns like Hamilton's PRP, or Polymer Labs PLRP.

Alternatively, ethanol precipitation, diafiltration, or gel filtration may be used followed by lyophilization or solvent evaporation under vacuum in commercially available instrumentation such as Savant's Speed Vac. Optionally, small amounts of the oligonucleotides may be electrophoretically purified using polyacrylamide gels.

Lyophilized or dried own preparations of oligonucleotides can be dissolved in pyrogen-free, sterile, physiological saline (i.e., 0.85% saline), sterile Sigma water, and filtered through a 0.45 micron Gelman filter (or a sterile 0.2 micron pyrogen-free filter). The described oligonucleotides may be partially or fully substituted with any of a broad variety of chemical groups or linkages including, but not limited to: phosphoramidates; phosphorothioates; alkyl phosphonates; 2'-O-methyls; 2'-modified RNAs; morpholino groups; phosphate esters; propyne groups; or chimerics of any combination of the above groups or other linkages (or analogs thereof).

A variety of standard methods can be used to purify the presently described oligonucleotides. In brief, the oligonucleotides of the present invention can be purified by chromatography on commercially available reverse phase (for example, see the RAINS Instrument Co., Inc. instruction manual for the DYNAMAX®-300A, Pure-DNA reverse-phase columns, 1989, or current updates thereof, herein incorporated by reference) or ion exchange media such as Waters' Protein Pal or Pharmacia's Source Q (see generally, Warren and Vella, 1994, "Analysis and Purification of Synthetic Nucleic Acids by High-Performance Liquid Chromatography", in *Methods in Molecular Biology*, vol. 26; *Protocolsfor Nucleic Acid Conjugates*, S. Agrawal, Ed., Humana Press, Inc., Totowa, N.J.; Aharon et al., 1993, *J. Chrom.* 698:293–301; and Millipore Technical Bulletin, 1992, *Antisense DNA: Synthesis, Purification, and Analysis*). Peak fractions can be combined and the samples concentrated and desalted via alcohol (ethanol, butanol, isopropanol, and isomers and mixtures thereof, etc.) precipitation, reverse phase chromatography, diafiltration, or gel filtration.

The modified polynucleotides and oligonucleotides that are associated on the array may also be produced used established techniques such as polymerase chain reaction (PCR) and reverse transcription (RT). These methods are similar to those currently known in the art (see e.g., *PCR Strategies*, Michael A. Innis (Editor), et al. (1995) and PCR:Introduction to Biotechniques Series, C. R. Newton, A. Graham (1997)), and preferably the enzymes used to produce the polynucleotides or oligonucleotides are optimized for incorporation of modified nucleotide monomers. Methods of identifying which enzymes are best suited for incorporation of nucleotide monomers with specific modifications (e.g., which enzymes will best incorporate 2'-modified dNTPs) are well known in the art, and thus one skilled in the art would be able to identify enzymes for use with the present invention based upon this disclosure. For example, the process directed evolution can be used to unveil mechanisms of both thermal adaptation and incorporation efficiency, and is an effective and efficient approach to identifying optimal enzyme activity. Multiple generations of random mutagenesis, recombination and high throughput can be used to create a polymerase that both incorporates modified nucleotide monomers, e.g., 2'-O-methyl substituted dNTPs, and remains thermostable at higher temperatures. See e.g., Zhao H, et al. 12:47–53 (1999).

Other methods of altering catalytic activity include site-directed mutagenesis, codon-level mutagenesis and methods of incorporating deletions or insertions into available enzymes. Genomic sequencing programs may also reveal conserved regions in the enzyme structure and regions of variability between enzymes from closely related species, thus identifying regions of an enzyme that may be altered without affecting the desired activity. It would be well within the skill of one in the art to use such techniques to identify an enzyme with optimal performance for producing the modified polynucleotides and oligonucleotides of the invention.

Techniques for identification of specific enzymes for production of polynucleotides for association on the arrays of the invention are described in Schmidt-Dannert C, et al., *Trends Biotechnol.* 17:135–6 (1999); Moreno-Hagelsieb G, et al., *Biol Res.*29:127–40 (1996); Colacino F, et al., *Biotechnol Genet Eng Rev.* 14:211–77 (1997); Soberon X. *Nat Biotechnol.* 17:539–40 (1999); Arnold FH, et al., *Ann N Y Acad Sci.* 870:400–3 (1999); and Joo H, et al., *Nature* 399:670–3 (1999), each of which are incorporated herein by reference to describe such techniques and enzyme design.

An oligonucleotide or polynucleotide is considered pure when it has been isolated so as to be substantially free of, inter alia, incomplete products produced during the synthesis of the desired oligonucleotide or polynucleotide. Preferably, a purified oligonucleotide or polynucleotide will also be substantially free of contaminants which may hinder or otherwise mask the binding activity of the molecule.

ARRAY CONSTRUCTION

The arrays of the subject invention have a plurality of associated modified oligonucleotides and/or polynucleotides stably associated with a surface of a solid support, e.g., covalently attached to the surface with or without a linker molecule. Each associated sample on the array comprises a modified oligonucleotide composition, of known identity, usually of known sequence, as described in greater detail below. Any conceivable substrate may be employed in the invention.

In the arrays of the invention, the modified oligonucleotide compositions are stably associated with the surface of a solid support, where the support may be a flexible or rigid solid support. By "stably associated" is meant that the sample of associated modified oligonucleotides and/or polynucleotides maintain their position relative to the solid support under hybridization and washing conditions. As such, the samples can be non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the oligonucleotides and a functional group present on the surface of the rigid support (e.g., —OH), where the functional group may be naturally occurring or present as a member of an introduced linking group, as' described in greater detail below.

As mentioned above, the array is present on either a flexible or rigid substrate. A flexible substrate is capable of being bent, folded or similarly manipulated without breakage. Examples of solid materials which are flexible solid supports with respect to the present invention include membranes, e.g., nylon, flexible plastic films, and the like. By "rigid" is meant that the support is solid and does not readily bend, i.e., the support is not flexible. As such, the rigid substrates of the subject arrays are sufficient to provide physical support and structure to the associated oligonucleotides and/or polynucleotides present thereon under the assay conditions in which the array is employed, particularly under high throughput handling conditions. Furthermore, when the rigid supports of the subject invention are bent, they are prone to breakage.

The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc.

The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface are also chosen to provide appropriate light-absorbing characteristics. For instance, the substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure.

In a preferred embodiment the substrate is flat glass or single-crystal silicon with surface relief features of less than 10 angstroms. According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, etc.

Surfaces on the solid substrate will usually, though not always, be composed of the same material as the substrate. Alternatively, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which could be carboxyl, amino, hydroxyl, or the like. Most preferably, the surface will be optically transparent and will have surface Si—OH functionalities, such as are found on silica surfaces.

The surface of the substrate is preferably provided with a layer of linker molecules, although it will be understood that the linker molecules are not required elements of the invention. The linker molecules are preferably of sufficient length to permit modified oligonucleotides and/or polynucleotides of the invention and on a substrate to hybridize to natural nucleic acid molecules and to interact freely with molecules exposed to the substrate. The linker molecules should be 6–50 atoms long to provide sufficient exposure. The linker molecules may also be, for example, aryl acetylene, ethylene glycol oligomers containing 2–10 monomer units, diamines, diacids, amino acids, or combinations thereof. Other linker molecules which can bind to modified oligonucleotides of the invention may be used in light of this disclosure.

The linker molecules can be attached to the substrate via carbon—carbon bonds using, for example, (poly) trifluorochloroethylene surfaces, or preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized Langtmuir Blodgett film. In alternative embodiments, the linker molecules are adsorbed to the surface of the substrate.

In one embodiment of the present invention, the linker molecules and modified nucleotides used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating. The protective group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxycarbonyl (NVOC), 2-nitrobenzyloxycarbonyl (NBOC) or $\alpha,\alpha$-dimethyl-dimethoxybenzyloxycarbonyl (DDZ) is used. Photoremovable protective groups are described in, for example, Patchornik, *J. Am. Chem. Soc.* (1970) 92:6333 and Amit et al., *J. Org. Chem.* (1974) 39:192, both of which are incorporated herein by reference.

The substrate, the region for attachment of an individual oligonucleotide group could be of any size or shape. For example, squares, ellipsoids, rectangles, triangles, circles, or portions thereof, along with irregular geometric shapes, may be utilized. Duplicate synthesis regions may also be applied to a single substrate for purposes of redundancy. The regions on the substrate can have a surface area of between about 1 cm$^2$ and 10$^{-10}$ cm$^2$. Preferably, the regions have areas of less than about 10$^{-1}$ to 10$^{-7}$ cm$^2$, more preferably less than 10$^{-3}$ to 10$^{-6}$ cm$^2$, and even more preferably less than 10$^{-5}$ cm$^2$.

A single substrate supports more than about 10 different oligonucleotide and/or polynucleotide compositions and preferably more than about 100 different oligonucleotide and/or polynucleotide compositions, although in some embodiments more than about 10$^3$, 10$^4$, 10$_5$, 10$^6$, 10$^7$, or 10$^8$ different compositions are provided on a substrate. In a preferred embodiment, the number of oligonucleotide compositions on an array ranges from about 2 to about 10$^9$. Of course, within a region of the substrate in which a modified oligonucleotide or polynucleotide is attached, it is preferred that the modified nucleotides be substantially pure. In preferred embodiments, regions of the substrate contain oligonucleotides or polynucleotides which are at least about 50%, preferably 80%, more preferably 90%, and even more preferably, 95% pure. Oligonucleotides or polynucleotides having several sequences can be intentionally provided within a single region so as to provide an initial screening for biological activity, after which materials within regions exhibiting significant binding are further evaluated. In a preferred embodiment, each region will contain a substantially pure modified oligonucleotide or polynucleotide composition having a single sequence.

The substrates of the arrays of the invention comprise at least one surface on which the pattern of associated oligonucleotides and/or polynucleotides is present, where the surface may be smooth, substantially planar, or have irregularities, such as depressions or elevations. The surface on which the pattern of associated nucleic acids present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like.

The amount of modified oligonucleotide or polynucleotide present in each composition will be sufficient to provide for adequate hybridization and detection of nucleic acids during the assay in which the array is employed. Generally, the amount of oligonucleotide or polynucleotide in each composition will be at least about 0.1 ng, usually at least about 0.5 ng and more usually at least about 1 ng, where the amount may be as high as 1000 ng or higher, but will usually not exceed about 20 ng and more usually will not exceed about 10 ng. The copy number of each oligonucleotide or polynucleotide in a composition will be sufficient to provide enough hybridization sites to yield a detectable signal, and will generally range from about 0.01 fmol to 50 fmol, usually from about 0.05 fmol to 20 fmol and more usually from about 0.1 fmol to 5 fmol. Where the composition has an overall circular dimension, the diameter of the sample will generally range from about 10 to 5,000 $\mu$m, usually from about 20 to 2,000 $\mu$m and more usually from about 50 to 1000 $\mu$m.

Control composition may be present on the array including compositions comprising oligonucleotides or polynucleotides corresponding to genomic DNA, housekeeping genes, negative and positive control genes, and the like. These latter types of compositions are not "unique" as that term is defined and used herein, i.e., they are "common." In other words, they are calibrating or control genes whose function is not to tell whether a particular "key" gene of interest is expressed, but rather to provide other useful information, such as background or basal level of expression. The percentage of samples which are made of unique oligonucleotides or polynucleotide that correspond to the same type of gene is generally at least about 30%, and usually at least about 60% and more usually at least about 80%. Preferably, the arrays of the present invention will be of a specific type, where representative array types include: human arrays, mouse arrays, cancer arrays, apoptosis arrays, human stress arrays, oncogene and tumor suppressor arrays, cell—cell interaction arrays, cytokine and cytokine receptor arrays, rat arrays, blood arrays, mouse stress arrays, neuroarrays, and the like.

With respect to the oligonucleotide and/or polynucleotide compositions that correspond to a particular type or kind of gene, type or kind can refer to a plurality of different characterizing features, where such features include: species specific genes, where specific species of interest include eukaryotic species, such as mice, rats, rabbits, pigs, primates, humans, etc.; function specific genes, where such genes include oncogenes, apoptosis genes, cytokines, receptors, protein kinases, etc.; genes specific for or involved in a particular biological process, such as apoptosis, differentiation, cell cycle regulation, cancer, aging, proliferation, etc.; location specific genes, where locations include organs, such as heart, liver, prostate, lung etc.; tissue, such as nerve, muscle, connective, etc.; cellular, such as axonal, lymphocytic, etc.; or subcellular locations, e.g., nucleus, endoplasmic reticulum, Golgi complex, endosome, lyosome, peroxisome, mitochondria, cytoplasm, cytoskeleton, plasma membrane, extracellular space; specific genes that change expression level over time, e.g., genes that are expressed at different levels during the progression of a disease condition, such as prostate genes which are induced or repressed during the progression of prostate cancer.

In a preferred embodiment, longer oligonucleotides, preferably from 80–300 nt in length, more preferably from 100–200 nt in length, are used on the arrays. These are especially useful in place of cDNAs for determining the presence of mRNA in a sample, as the modified oligonucleotides have the advantage of rapid synthesis and purification and analysis prior to attachments to the substrate surface. In particular, oligonucleotides with 2' modified sugar groups show increased binding affinity with RNA, and these oligonucleotides are particularly advantageous in identifying mRNA in a sample exposed to an array.

The length of the modified oligonucleotides allows the compositions to bind with the same affinity as a much longer unmodified nucleic acid, e.g. an unmodified cDNA. In the case where additional complementarity is needed to certain domains or regions found in cDNA, multiple oligonucleotides may be used. Multiple oligonucleotides directed at a particular gene or RNA molecule may be interspersed in a single region, or the different oligonucleotides may each be in a discrete region, e.g. to determine presence or absence of related molecules in a sample.

As mentioned above, the arrays of the present invention typically comprise one or more additional associated oligonucleotide composition which does not correspond to the array type, i.e., the type or kind of gene represented on the array. In other words, the array may comprise one or more compositions that are made of non "unique" oligonucleotides, e.g., oligonucleotides corresponding to commonly expressed genes. For example, compositions comprising oligonucleotides that bind to plasmid and bacteriophage oligonucleotides, oligonucleotides which bind to genes from the same or another species which are not expressed and do not cross-hybridize with the test nucleic acid, and the like, may be present and serve as negative controls. In addition, compositions comprising housekeeping genes and other control genes from the same or another species may be present, e.g., to serve in the normalization of mRNA abundance and standardization of hybridization signal intensity in the sample assayed with the array.

Patents and patent applications describing arrays of oligonucleotides and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; 5,700,637; 5,744,305; 5,837,832; 5,843,655; 5,861,242; 5,874,974; 5,885,837; WO 93/17126; WO 95/11995; WO 95/35505; EP 742 287; and EP 799 897. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; 5,874,219; WO 95/21265; WO 96/31622; WO 97/10365; WO 97/27317; EP 373 203; and EP 785 280.

References that disclose the synthesis of arrays and reagents for use with arrays include: Matteucci M. D. and Caruthers M. H., *J. Am. Chem. Soc.* (1981) 103:3185–3191; Beaucage S. L. and Caruthers M. H., *Tetrahedron Letters*, (1981) 22(20):1859–1862; Adams S. P. et al., *J. Am. Chem. Soc.* (1983) 105:661–663; Sproat D. S. and Brown D. M., *Nucleic Acids Research*, (1985) 13(8):2979–2987; Crea R. and Horn T., *Nucleic Acids Research*, (1980) 8(10):2331–48; Andrus A. et al., *Tetrahedron Letters*, (1988) 29(8):861–4; Applied Biosystems User Bulletin, Issue No. 43, Oct. 1, 1987, "Methyl phosphonamidite reagents and the synthesis and purification of methyl phosphonate analogs of DNA"; Miller P. S. et al., *Nucleic Acids Research*, (1983) 11:6225–6242. Each of these is incorporated herein by reference as exemplary methods of construction and use of arrays of the present invention. The methods of these publications can be readily modified to produce the arrays of the invention with the modified oligonucleotides of the invention on their surface.

In a preferred embodiment, the modified oligonucleotides for use with the present invention are synthesized prior to attachment onto the substrate. This affords the advantages that: (1) oligonucleotides of known composition and sequence can be produced; (2) oligonucleotides can be analyzed and purified prior to attachment, which eliminates "shortmers," i.e., oligonucleotides with insufficient length and/or incorrect sequence; (3) the methods used to produce oligonucleotides are less prone to error than current methods for production of cDNA, e.g. PCR with Taq polymerase, and (4) attachment to the substrate may be monitored or assayed without destroying the array.

Numerous methods can be used for attachment of the oligonucleotides of the invention to the substrate. For example, modified oligonucleotides can be attached using the techniques of, for example U.S. Pat. No. 5,807,522, which is incorporated herein by reference for teaching methods of polymer attachment. Other similar methods may be used, as will be apparent to one skilled in the art upon reading the present technology.

USE OF ARRAYS OF THE INVENTION

Oligonucleotide and/or polynucleotide arrays provide a high throughput technique that can assay a large number of polynucleotides in a sample. A variety of different array formats have been developed and are known to those of skill in the art. The arrays of the subject invention find use in a variety of applications, including gene expression analysis, drug screening, mutation analysis and the like.

Arrays can be used, for example, to examine differential expression of genes and can be used to determine gene function. For example, arrays can be used to detect differential expression of a polynucleotide between a test cell and control cell (e.g., cancer cells and normal cells). For example, high expression of a particular message in a cancer cell, which is not observed in a corresponding normal cell, can indicate a cancer specific gene product. Exemplary uses of arrays are further described in, for example, Pappalarado et al., *Sem. Radiation Oncol.* 8:217 (1998), and Ramsay, *Nature Biotechnol.* 16:40 (1998).

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data can be displayed as an image with the intensity in each region varying according to the binding affinity between associated oligonucleotides and/or polynucleotides and the test nucleic acids.

Oligonucleotides having a sequence unique to that gene are preferably used in the present invention. Different methods may be employed to choose the specific region of the gene to be targeted. A rational design approach may also be employed to choose the optimal oligonucleotide sequence for the hybridization array. Preferably, the region of the gene that is selected is chosen based on the following criteria First, the sequence that is chosen should yield an oligonucleotide composition that preferably does not cross-hybridize with any other oligonucleotide composition present on the array. Second, the sequence should be chosen such that the oligonucleotide composition has a low probability of cross-hybridizing with an oligonucleotide having a nucleotide sequence found in any other gene, whether or not the gene is to be represented on the array from the same species of origin, e.g., for a human array, the sequence will not be present in any other human genes. As such, sequences that are avoided include those found in: highly expressed gene products, structural RNAs, repeated sequences found in the sample to be tested with the array and sequences found in vectors. A further consideration is to select oligonucleotides with sequences that provide for minimal or no secondary structure, structure which allows for optimal hybridization but low non-specific binding, equal or similar thermal stabilities, and optimal hybridization characteristics.

EXEMPLARY ARRAY TYPES OF THE INVENTION

A variety of specific array types are also provided by the subject invention. As discussed above, array type refers to the nature of the oligonucleotide and/or polynucleotide compositions present on the array and the types of genes to which the associated compositions correspond These array types include, but are not limited to: human array; mouse array; developmental array; cancer array, apoptosis array; oncogene and tumor suppressor array; cell cycle gene array, cytokine and cytokine receptor array; growth factor and growth factor receptor array; neuroarrays; and the like.

In certain embodiments of the human array, human genes that may be represented by the composition on the arrays include those for: (a) oncogenes and tumor suppressors; (b) cell cycle regulators; (c) stress response proteins; (d) ion channel and transport proteins; (e) intracellular signal transduction modulators and effectors; (f) apoptosis-related proteins; (g) DNA synthesis, repair and recombination proteins; (h) transcription factors and general DNA binding proteins; (i) growth factor and chemokine receptors; (j) interleukin and interferon receptors; (k) hormone receptors; (l) neurotransmitter receptors; (m) cell surface antigens and cell adhesion proteins; (n) growth factors, cytokines and chemokines; (o) interleukins and interferons; (p) hormones; (q) extracellular matrix proteins; (r) cytoskeleton and motility proteins; (s) RNA processing and turnover proteins; (t) post-translational modification, trafficking and targeting proteins; (u) protein turnover, and (v) metabolic pathway proteins.

The arrays of the invention can be used in, among other applications, differential gene expression assays. Thus, arrays are useful in the differential expression analysis of: (a) diseased and normal tissue, e.g., neoplastic and normal tissue, (b) different tissue or tissue types; (c) developmental stage; (d) response to external or internal stimulus; (e) response to treatment; and the like. The arrays are also useful in broad scale expression screening for drug discovery and research, such as the effect of a particular active agent on the expression pattern of genes in a particular cell, where such information can be used to reveal drug toxicity, carcinogenicity, etc., environmental monitoring, disease research and the like.

HYBRIDIZATION AND DETECTION

Following preparation of the test nucleic acids from the tissue or cell of interest, the test sample is contacted with the array under hybridization conditions, where such conditions can be adjusted, as desired, to provide for an optimum level of specificity in view of the particular assay being performed. In analyzing the differences in the population of labeled test binding agents generated from two or more physiological sources using the arrays described above, each population of labeled test samples are separately contacted to identical arrays or together to the same array under conditions of hybridization, preferably under stringent hybridization conditions (for example, at 50° C. or higher and 0.1×SSC (15 mM sodium chloride/01.5 mM sodium citrate)), such that test nucleic acids hybridize to complementary oligonucleotides and/or polynucleotides on the substrate surface.

Where all of the test nucleic acids have the same label, different arrays can be employed for each physiological source. Preferably, the same array can be employed sequentially for each physiological source, with test samples removed from the array as described below. Alternatively, where the labels of the test nucleic acids are different and distinguishable for each of the different physiological sources being assayed, the opportunity arises to use the same array at the same time for each of the different test populations. Examples of distinguishable labels are well known in the art and include: two or more different emission wavelength fluorescent dyes, like Cy3 and Cy5, two or more isotopes with different energies of emission, like $^{32}$P and $^{33}$P, labels which generate signals under different treatment conditions, like temperature, pH, treatment by additional chemical agents, etc., or generate signals at different time points after treatment. Using one or more enzymes for signal generation allows for the use of an even greater variety of distinguishable labels, based on different substrate specificity of enzymes (e.g., alkaline phosphatase/peroxidase).

Following hybridization, non-hybridized labeled nucleic acid is removed from the support surface, conveniently by washing, generating a pattern of hybridized oligonucleotide and/or polynucleotide on the substrate surface. A variety of wash solutions are known to those of skill in the art and may be used. The resultant hybridization patterns of labeled, hybridized oligonucleotides and/or polynucleotides may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Following detection or visualization, the hybridization patterns may be compared to identify differences between the patterns. Where arrays in which each of the different oligonucleotides and/or polynucleotides corresponds to a known gene are employed, any discrepancies can be related to a differential expression of a particular gene in the physiological sources being compared.

CLEARING OF TEST NUCLEIC ACIDS FROM ARRAY

Following binding and visualization of a test sample on an array, the array may be treated to remove the bound test nucleic acids. The associated nucleic acid compositions remain intact following treatment, allowing reuse of the treated array. The array of the invention substantially retains its binding capabilities, and any differences in binding ability may be determined using control sequences associated on the array. Preferably, the array of the invention retains at least 75% of its binding capabilities, more preferably the array retains at least 85% of its binding capabilities, and even more preferably the array of the invention retains at least 95% of its binding capabilities.

Arrays with associated modified oligonucleotide and/or polynucleotide compositions can be exposed to a low pH environment, e.g., pH from 0.5–4.5, which results in the degradation of non-modified nucleic acids. Following the treatment, the arrays of the invention are rinsed to remove any unwanted test nucleic acid fragments, residual label and the like, and the arrays are prepared for reuse.

After detection of the test sample is complete, the array may be regenerated by removal and/or degradation of the test sample. For example, a two hour incubation of the sample-bound array in an acid solution at pH 1.5, 39° C., results in complete loss of a full-length unmodified 14-mer oligonucleotide. Under these conditions the bound array oligonucleotides of the invention maintain full length structural integrity. Following the acid incubation, a variety of wash conditions may be used to clear the test sample from the probe array. For example, increased temperature incubation of a low salt wash solution would result in the dissociation of short test fragments from the array. Alternatively, a chemical denaturant (e.g. urea) could be used as a wash to remove the test sample. Additional steps, such as an alkaline solution rinse may also be added to the protocol to speed up the cycle time for regeneration.

The above-described washes and rinses can be avoided if the acid incubation is increased resulting in almost complete degradation of the test sample under conditions where the array probe maintains its integrity. Actual incubation times required will vary somewhat from array type to array type, and may be shorter than those given below. As a consequence of the degradation of the test sample the array probe/test sample hybrids become unstable under experimental conditions and may be removed using rinses of the hybridization or stringent wash buffer.

Exemplary clearing conditions for use with the arrays of the invention are:

(1) Incubation of the bound array with pH 1–2 acid solution, 8 hours at 39° C. Follow with three rinses at 39° C. with stringent wash buffer, 0.1×SSC pH 7.0, and two rinses with hybridization buffer, pH approximately 7.0. These two solutions are for removal of degraded sample and the regeneration of the substrate array and hence do not require a low pH. Array may then be reused.

(2) Incubation of the bound array with pH 1–2 acid solution, 4 hours at 39° C. Follow with three 15 minute rinses at 39° C. with 8.0 molar urea. Rinse once with stringent wash buffer, and twice with hybridization buffer. Array can be reused at this point.

(3) Incubation of the bound array with pH 1–2 acid solution, 4 hours at 39° C. Rinse twice at 39° C. with stringent wash buffer. Incubate 20 minutes in 60° C. stringent wash buffer, and rinse twice more with 60° C. stringent wash buffer. Rinse twice with hybridization buffer. Array can be reused at this point.

(4) Incubation of the bound array with pH 1–2 acid solution, 4 hours at 39° C. Rinse twice with stringent wash buffer. Wash twice with 39° C. alkaline solution for 15 minutes followed by two washes with stringent wash buffer. Incubate 20 minutes in 60° C. stringent wash buffer. Rinse twice more with 60° C. stringent wash buffer, and twice with hybridization buffer. Array can be reused at this point.

(5) Incubation of the bound array with nuclease (actual conditions vary with nuclease type) at 37° C. for 1 hour. Wash twice with protein denaturing solution for 20 minutes. Rinse twice with stringent wash buffer. Incubate 20 minutes in 60° C. stringent wash buffer. Rinse twice with 60° C. stringent wash buffer. Rinse twice with hybridization buffer. Array can be reused at this point.

(6) Incubation of the bound array with pH 10–13 base solution (e.g., NaOH) at room temperature for 1–30 minutes followed by additional washes with pH 10–13 base solutions, water, or acidic solution washes followed by a buffer wash.

Following treatment, the associated acid stable oligonucleotides of the array remain 1) associated to the substrate surface; 2) structurally intact; and 3) capable of binding with another test binding partner.

In addition, as an alternative way, arrays with associated oligonucleotides characterized as nuclease resistant may be treated with a nuclease to remove bound test nucleic acids and label. The nuclease used can be chosen depending on the nature of the binding between the associated oligonucleotide and/or polynucleotide and the molecules of the test sample and the attachment of the oligonucleotide and/or polynucleotide to the array. For example, if the associated oligonucleotides are end-blocked oligonucleotides, and the test sample is comprised of mRNA molecules, then the appropriate nuclease would be one that recognizes RNA-DNA hybrids, e.g.; Ribonuclease H. In another example, if the associated oligonucleotides are end-blocked oligonucleotides, and the test sample is comprised of cDNA molecules, then the appropriate nuclease would be one that recognizes double stranded DNA complexes, e.g., Deoxyribonuclease I or II, and Exodeoxyribonuclease III or V. In yet another example, if the associated oligonucleotides are end-blocked cRNA and the test sample is comprised of mRNA, the appropriate nuclease is one that recognizes RNA—RNA hybrids, such as micrococcal nuclease. Similarly, nucleases that are 5' or 3' specific may be chosen depending on the attachment site of the oligonucleotide and/or polynucleotide to the array. Since the oligonucleotides of this embodiment of the invention are nuclease-resistant, the test samples will be specifically targeted and degraded by the nuclease.

Actual choice of regeneration conditions should take into consideration the type of substrate, the type of attachment of probe to substrate, test sample type, and whether there are clearing time constraints. In cases where the substrate is acid sensitive it would be more advantageous to use nuclease digestion to remove the test sample from the array. Such modifications would be well within the skill of one in the art upon reading the present disclosure and description of the subject arrays.

KITS HAVING ARRAYS OF PRESENT INVENTION

Also covered are kits for performing analyte binding assays using the arrays of the present invention. Such kits according to the subject invention will at least comprise the arrays of the invention having associated modified oligonucleotides and/or polynucleotides. Kits also preferably comprise an agent for removal of test binding agents, e.g., a solution with low pH and/or with nuclease activity. The kits may further comprise one or more additional reagents employed in the various methods, such as: 1) primers for generating test nucleic acids; 2) dNTPs and/or rNTPs (either premixed or separate), optionally with one or more uniquely labeled dNTPs and/or rNTPs (e.g., biotinylated or Cy3 or Cy5 tagged dNTPs); 3) post synthesis labeling reagents, such as chemically active derivatives of fluorescent dyes; 4) enzymes, such as reverse transcriptases, DNA polymerases, and the like; 5) various buffer mediums, e.g., hybridization and washing buffers; 6) labeled probe purification reagents and components, like spin columns, etc.; and 7) signal generation and detection reagents, e.g., streptavidin-alkaline phosphatase conjugate, chemifluorescent or chemiluminescent substrate, and the like.

EXAMPLES

The present invention and its particular embodiments are illustrated in the following examples. The examples are not intended to limit the scope of this invention but are presented to illustrate and support the claims of this present invention.

Example 1

Synthesis and Purification of Modified Nucleic Acids

Oligonucleotides were synthesized using commercial phosphoramidites on commercially purchased DNA synthesizers from <1 uM to >1 mM scales using standard phosphoramidite chemistry and methods that are well known in the art, such as, for example, those disclosed in Stec et al., J. Am. Chem. Soc. 106:6077–6089 (1984), Stec et al., J. Org. Chem. 50(20):3908–3913 (1985), Stec et al., J. Chromatog. 326:263–280 (1985), LaPlanche et al., Nuc. Acid. Res. 14(22):9081–9093 (1986), and Fasman, Practical Handbook of Biochemistry and Molecular Biology, 1989, CRC Press, Boca Raton, Fla., herein incorporated by reference.

Oligonucleotides were deprotected following phosphoramidite manufacturer's protocols. Unpurified oligonucleotides were either dried down under vacuum or precipitated and then dried. Sodium salts of oligonucleotides were prepared using the commercially available DNA-Mate (Barkosigan Inc.) reagents or conventional techniques such as commercially available exchange resin, e.g., Dowex, or by addition of sodium salts followed by precipitation, diafiltration, or gel filtration, etc.

A variety of standard methods were used to purify and produce the presently described oligonucleotides. In brief, oligonucleotides were purified by chromatography on commercially available reverse phase (for example, see the RAININ Instrument Co., Inc. instruction manual for the DYNAMAX®-300A, Pure-DNA reverse-phase columns, 1989, or current updates thereof, herein incorporated by reference) or ion exchange media such as Waters' Protein Pak or Pharmacia's Source Q (see generally Warren and Vella, 1994, "Analysis and Purification of Synthetic Nucleic Acids by High-Performance Liquid Chromatography", in Methods in Molecular Biology, vol. 26; Protocols for Nucleic Acid Conjugates, S. Agrawal, Ed. Humana Press, Inc., Totowa, N.J.; Aharon et al., 1993, J Chrom. 698:293–301; and Millipore Technical Bulletin, 1992, Antisense DNA: Synthesis, Purification, and Analysis). Peak fractions were combined and the samples were concentrated and desalted via alcohol (ethanol, butanol, isopropanol, and isomers and mixtures thereof, etc.) precipitation, reverse phase chromatography, diafiltration, or gel filtration or size-exclusion chromatography.

Lyophilized or dried-down preparations of oligonucleotides were dissolved in pyrogen-free, sterile, physiological saline (i.e., 0.85% saline), sterile Sigma water, and filtered through a 0.45 micron Gelman filter.

Example 2

Stability of Modified Oligonucleotide Duplexes

The stability of duplexes having 2'-substituted nucleotides versus duplexes without such modification was tested by examining the $T_m$ of these complexes. 4 µM each of 20-mer oligonucleotide (5'-ggt ggt tcc tcc tca gtc gg-3'; SEQ ID NO:1) and its complement (5'- ccg act gag aag gaa cca cc-3;SEQ ID NO:2) were bound in a solution of 50 mM NaCl, 10 mM PO4 buffer, pH 7.4. Each of the nucleotides of the oligonucleotide had the same 2' group. Following binding, the melting temperature was determined as described. (See L. L. Cummins et al., Nucleic Acids Research 23:2019–2024 (1995).

| SEQ ID NO:1 | SEQ ID NO:2 | $T_m$ |
|---|---|---|
| Regular RNA and | Regular DNA | 66° C. |
| Regular RNA and | 2'-O-methyl | 79° C. |
| Regular DNA and | p-ethoxy DNA | 55° C. |
| Regular RNA and | p-ethoxy RNA | 56° C. |
| Regular RNA and | p-ethoxy 2'-O-methyl | 71° C. |

The duplexes with the 2'-O-methyl substitutions display a significantly increased $T_m$ compared to RNA or DNA with a 2' H or 2' OH, respectively. RNA or DNA with propyl or fluoro substitutions at the 2' position display an even higher $T_m$ than does the 2'-O-methyl.

Example 3

Acid Stability of the Oligonucleotides of the Invention

Homopolymers of 2'-O-methyl A, C, G, and U twelve bases long, were synthesized with 3' and 5' inverted T-blocked ends. They were purified, desalted, lyophilized, and dissolved at 300 $A_{260}$ per ml in sterile water. Samples were removed and diluted 1 to 4 with either 0.1 N HCl or 1.0 N HCl to give final pHs of approximately 1 and 0, respectively, and placed in a heat block at 39° C. Aliquots were taken at 0, 2, 4 and 24 hours, diluted 1:20 into a solution of 0.025 M NaOH and 0.03 M NaCl, stored at −20° C. until being run on an analytical HPLC under strongly denaturing conditions on an anion exchange column.

| | | % Full Length | | | |
|---|---|---|---|---|---|
| Homopolymer | pH | 0 hr | 2 hr | 4 hr | 24 hr |
| A | 1 | 99 | 99 | 99 | 99 |
| C | 1 | 99 | 99 | 99 | 96 |
| G | 1 | 96 | 98 | 98 | 98 |
| U | 1 | 97 | — | 97 | 97 |
| A | 0 | 99 | 99 | 99 | 99 |
| C | 0 | 99 | 99 | 98 | 97 |
| G | 0 | 96 | 97 | 97 | 89 |
| U | 0 | 97 | — | 97 | 96 |

It was evident that there is essentially no degradation at pH 1 and 39° C. and only slight degradation over 24 hours at pH 0 and 39° C.

Example 4

Acid Stability of the Oligonucleotides of the Invention

A 14 mer heteropolymer was synthesized as a regular phosphodiester DNA (O), a phosphorothioate DNA (S), an unblocked 2'-O-methyl RNA (2'om), a 2'-O-methyl RNA with 3' and 5' butanol blocked ends (B2'om), and a phosphorothioate chimera having four 2'-O-methyl phosphorothioate bases on either side of 6 interior phosphorothioate DNA bases (SD). They were purified, desalted, lyophilized, and dissolved at 300 $A_{260}$ per ml in sterile water. Samples were removed and diluted 1 to 4 with 0.1 N HCl to give a final pH of approximately 1.5, and placed in a heat block at 39° C. Aliquots were taken at the times indicated and diluted 1:20 into a solution of 0.025 M NaOH and 0.03 M NaCl, and were run on an analytical HPLC under strongly denaturing conditions on an anion exchange column. Initially all but the end-blocked 2'-O-methyl RNA solutions became cloudy upon addition of the HCl. Upon heating, both the phosphodiester DNA and the unblocked 2'-O-methyl RNA became clear. The two oligonucleotides with phosphorothioate linkages appeared cloudy until about 2 hours when they slowly began to clear as they decomposed.

| | % Full Length | | | | | | | | | | |
|---|---|---|---|---|---|---|---|---|---|---|---|
| Oligo | 0 hr | 0.5 hr | 1.0 hr | 2 hr | 4 hr | 6 hr | 1 d | 2 d | 3 d | 5 d | 10 d | 20 d |
| O | 99 | 38 | 10 | 0 | 0 | 0 | 0 | — | — | — | — | — |
| S | 95 | 65 | 29 | 1 | 0 | 0 | 0 | — | — | — | — | — |
| SD | 97 | 83 | 70 | 49 | 0 | 0 | 0 | — | — | — | — | — |
| 2'om | 99 | 99 | 99 | 99 | 98 | 98 | 98 | 96 | 94 | 94 | 87 | 80 |
| B2'om | 100 | 100 | 100 | 100 | 99 | 99 | 98 | 97 | 97 | 95 | 90 | 81 |

The 2'-O-methyl oligonucleotides, both unblocked and blocked, are far more stable than the corresponding phosphodiester, phosphorothioate, or a mixed 2'-O-methyl phosphorothioate structure that Agrawal et al. recommended to increase bioavailability.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An array comprising:
   (A) a support surface; and
   (B) a plurality of modified oligonucleotide compositions, each composition comprising a plurality of oligonucleotides stably associated with a distinct area of the support surface, wherein the oligonucleotides of each composition are characterized by:
   (1) independently having a length of from about 20 to about 300 nucleotides;
   (2) having internucleotide linkages selected from the group consisting of 2'-O-alkyl, 2'-O-alkyl-n(O-alkyl), combinations thereof;
   (3) having a binding affinity to a complementary sequence greater than the corresponding binding affinity of a non-modified oligonucleotide having the same sequence; and
   (4) having a pH stability of at least one hour at 37° C. at a pH in a range of about 0.5 to 6.

2. The array of claim 1, wherein the modified oligonucleotides further comprise an end block at the 3' end and exhibit exonuclease resistance of at least twice that of a naturally occurring oligonucleotide having the same sequence and number of bases.

3. The array of claim 1, wherein the modified oligonucleotides further comprise an end block at the 5' end and exhibit

SEQUENCE LISTING

```
<160> NUMBER OF SEQ ID NOS:  2

<210> SEQ ID NO 1
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 1
ggtggttcct cctcagtcgg                                            20

<210> SEQ ID NO 2
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 2
ccgactgaga aggaaccacc                                            20
``` exonuclease resistance of at least twice that of a naturally occurring oligonucleotide having the same sequence and number of bases.

4. An array of claim 1, wherein the modified oligonucleotides of each distinct area of the array exhibit substantially the same $T_m$.

5. The array of claim 1, wherein the modified oligonucleotides of a distinct area are selectively designed to hybridize to RNA.

6. The array of claim 1, wherein the modified oligonucleotides of a distinct area are selectively designed to hybridize to DNA.

7. The array of claim 1, wherein the modified oligonucleotides are further characterized by modification of at least 25% of their internucleoside linkages.

8. The array of claim 1, wherein said modified oligonucleotides have an average length of from about 100 to about 200 nucleotides.

9. The array of claim 1, wherein oligonucleotide sequences of the oligonucleotides of an oligonucleotide composition on the array differs from those of the oligonucleotides of any other oligonucleotide composition on said array.

10. The array of claim 1, wherein each oligonucleotide composition comprises a population of identical oligonucleotides.

11. The array of claim 1, wherein each oligonucleotide composition comprises a plurality of oligonucleotides that bind to a particular nucleic acid.

12. The array of claim 1, wherein the number of oligonucleotide compositions on said ranges from about 2 to about $10^9$ oligonucleotides.

* * * * *